United States Patent [19]
Ushio et al.

[11] Patent Number: 5,663,170
[45] Date of Patent: Sep. 2, 1997

[54] COMPOSITION FOR EYE DROPS

[75] Inventors: Kazumichi Ushio, Nishinomiya; Yoshifumi Ikejiri, Ibaraki, both of Japan

[73] Assignee: Senju Pharmaceutical Co., Ltd., Osaka, Japan

[21] Appl. No.: 912,580

[22] Filed: Jul. 13, 1992

Related U.S. Application Data

[63] Continuation of Ser. No. 743,811, Aug. 12, 1991, abandoned.

[30] Foreign Application Priority Data

Aug. 13, 1990 [JP] Japan ..................................... 2-214827
Jul. 3, 1991 [JP] Japan ..................................... 3-162854

[51] Int. Cl.$^6$ ..................................................... A61K 31/535
[52] U.S. Cl. ........................................ 514/231.2; 514/912
[58] Field of Search .................................. 514/224.2, 225, 514/228, 230.5, 772, 58

[56] References Cited

U.S. PATENT DOCUMENTS 4,771,050 9/1988 Meguro et al. ....................... 514/224.2

FOREIGN PATENT DOCUMENTS 3932925 2/1984 Japan.

*Primary Examiner*—Zohrer Fay
*Attorney, Agent, or Firm*—Wenderoth, Lind & Ponack

[57] ABSTRACT

A composition for eye drops comprising as a main effective component 3,4-dihydro-2,8-diisopropyl-3-thioxo-2H-1,4-benzoxadine-4-acetic acid or a pharmaceutically acceptable salt thereof and cyclodextrin is disclosed.

4 Claims, No Drawings

COMPOSITION FOR EYE DROPS

This application is a continuation of now abandoned application Ser. No. 07/743,811, filed Aug. 12, 1991.

FIELD OF THE INVENTION

The present invention relates to a composition for eye drops comprising as a main effective component 3,4-dihydro-2,8-diisopropyl-3-thioxo-2H-1,4-benzoxazine-4-acetic acid which causes no ocular irritation and is stable. More particularly, it relates to a composition for eye drops comprising cyclodextrin together with the above main effective component, optionally a water-soluble polymeric compound and, if necessary, a chelating agent and/or boric acid.

BACKGROUND OF THE INVENTION 3,4-Dihydro-2,8-diisopropyl-3-thioxo-2H-1,4-benzoxazine-4-acetic acid (hereinafter referred to as the "present compound") is, for example, as disclosed in U.S. Pat. No. 4,771,050, a compound having excellent aldose reductase inhibitory activity and platelet aggregation inhibitory activity and, further, is useful as a medicine for preventing and treating diabetic complication such as diabetic cataract, keratopathy, retinopathy, neuropathy, nephropathy and the like. Thus, the present compound can be used as a medicine in the field of ophthalmology, for example, diabetic cataract, keratopathy, retinopathy and the like as described above. On the other hand, for using a medicine in the field of ophthalmology, generally, it is desirable to apply the medicine by eye drops rather than by oral administration or injection from the viewpoint of side effects. However, if the present compound is formulated as eye drops, there are problems of stability, ocular irritation and the like, and the problems have not yet been solved until now.

When the present compound is formulated as eye drops for the purpose of treating diabetic cataract, retinopathy and the like, there are unavoidable disadvantages that stability on storage for a long period of time is insufficient and an undesirable insoluble material is formed in the resulting eye drops. Further, strong ocular irritation is caused when the present compound is applied by eye drops in the form of an aqueous solution. Therefore, although the present compound has excellent pharmacological activities, any practical eye drops containing it can not be obtained.

OBJECTS OF THE INVENTION

The main object of the present invention is to provide a composition for eye drops containing the present component which can be practically used.

This object as well as other objects and advantages of the present invention will become apparent to those skilled in the art from the following description.

SUMMARY OF THE INVENTION

The composition for eye drops of the present invention comprising as a main effective component the present compound, that is, 3,4-dihydro-2,8-diisopropyl-3-thioxo-2H-1,4-benzoxazine-4-acetic acid or a pharmaceutically acceptable salt thereof (in the following description, the term "the present compound" means "the present compound or a salt thereof" except in those instances where no salt is clearly intended from the context). The present compound is represented by the formula (I):

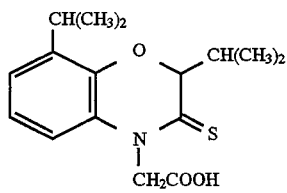

The present inventors have intensively studied so as to obtain a composition for eye drops containing the present compound, which causes no ocular irritation and is stable. As a result, it has been surprisingly found that, by formulating cyclodextrin and optionally a water-soluble polymeric compound, a composition for eye drops which causes no ocular irritation and is stable can be obtained. Further, it has been also found that, when a chelating agent and/or boric acid are further added to the composition, alleviation of ocular irritation and stability can be further improved. The present invention has been completed based on this finding.

That is, according to the present invention, there is provided (1) a composition for eye drops comprising as a main effective component 3,4-dihydro-2,8-diisopropyl-3-thioxo-2H-1,4-benzoxazine-4-acetic acid or a pharmaceutically acceptable salt thereof and cyclodextrin, (2) a composition of (1) further containing a water-soluble polymeric compound, (3) a composition of (2) further containing a chelating agent, and (4) a composition of (3) further containing boric acid.

DETAILED DESCRIPTION OF THE INVENTION

As described above, the present compound is disclosed in U.S. Pat. No. 4,771,050 and, for example, it can be conveniently produced according to the method disclosed in the above patent or modification thereof. In the present invention, the present compound may be used as a pharmaceutically acceptable salt thereof. Examples of the salt of the present compound include salts with alkali metals such as sodium, potassium and the like; salts with alkaline earth metals such as calcium, magnesium and the like; salts with aluminum and the like, and all of them can be suitably used.

The composition for eye drops of the present invention can be obtained by dissolving the present compound in water together with cyclodextrin. Examples of cyclodextrin include α-, β- and γ-cyclodextrin, and their derivatives. For the purpose of the present invention, β- or γ-cyclodextrin is preferred and, particularly, β-cyclodextrin is advantageously used.

The composition according to the present invention optionally contains a water-soluble polymeric compound in addition to cyclodextrin. As the water-soluble polymeric compound to be used is a pharmaceutically acceptable water-soluble polymeric compound which is effective for preventing formation of a water-insoluble matter. Particularly, a water-soluble polymeric compound which can provide viscosity to the composition is preferred and a water-soluble polymeric compound having an average molecular weight of about 5,000 to 5,000,000, preferably, about 10,000 to 1,000,000 is suitable. Examples thereof include polyvinyl pyrrolidone, polyvinyl alcohol, hydroxypropylmethyl cellulose, carboxypropylcellulose, hydroxyethyl cellulose, hydroxypropyl cellulose, sodium polyacrylate and the like. Among them, polyvinyl pyrrolidone, polyvinyl alcohol or hydroxypropylmethyl cellulose is preferred. Particularly, when using polyvinyl pyrrolidone having an average molecular weight of about 25,000 to 120,000, preferably about 40,000, good results can be obtained. When the water-soluble polymeric compound which can provide viscosity to the composition as described above is added, there is no need to add another kind of viscous agent to the composition of the present invention.

The concentration of the present compound in the composition of the present invention should be appropriately selected according to the type and the condition of ocular disease. For example, when the composition is applied to an adult patient of diabetes, the concentration is normally about 0.01 to 1 W/V %, and the composition is applied 3 to 5 times per day with 1 to a few drops per one application. The dosage can be appropriately changed according to a particular purpose.

The concentration of cyclodextrin and the water-soluble polymeric compound in the composition of the present invention may also be appropriately selected according to conditions of a particular patient, a concentration of the present compound and other conditions. In many cases, it is preferred that the amount of cyclodextrin is about 0.005 to 5W/V % and the amount of the water-soluble polymeric compound is about 0.2 to 20 W/V %.

In addition to the components as described above, a chelating agent can be formulated in the composition for eye drops according to the present invention. It is considered that the addition of the chelating agent is particularly effective for preventing formation of an insoluble matter in the composition of the present invention. As the chealting agent, there can be appropriately selected from chelating agents which are normally added to medicines, for example, disodium edetate, sodium citrate, condensed sodium phosphate and the like. The concentration of the chelating agent in the composition according to the present invention may also be appropriately selected according to conditions of a particular patient, a concentration of the present compound and other conditions. In many cases, it is preferred that the amount of the chelating agent is about 0.01 to 1 W/V %.

Boric acid may be further formulated in the composition for eye drops of the present invention. It is considered that the addition of boric acid is effective for obtaining the preservative activity and, further, is effective for stability and alleviation of ocular irritation. The concentration of boric acid in the composition according to the present invention may also be appropriately selected according to conditions of a particular patient, a concentration of the present compound and other conditions. In many cases, it is preferred that the amount of boric acid is about 0.2 to 4 W/V %, preferably about 0.5 to 3 W/V %. The use of boric acid is also preferred because it provides a buffering property to the composition of the present invention as described hereinafter.

In addition to the components described above, other ingredients which are normally used for eye drops can be formulated in the composition of the present invention unless interfering with the purpose of the present invention. Examples of such other ingredients include buffers, isotonizing agents, bactericides and the like. Examples of buffers include acetate buffer, phosphate buffer and the like. In the composition of the present invention, the chelating agent can be added as described above and, when sodium citrate is used as the chelating agent, it also acts as a buffer. Further, when boric acid is formulated in the composition, boric acid also acts as a buffer, and it is advantageous.

Further, an effective component other than the present compound may be formulated into the composition of the present invention unless interfering with the purpose of the present invention. Examples of such an effective component include an analgesic, an anti-inflammatory drug, an antiallergic drug, a wound healing drug, an antibiotic and the like.

In the composition for eye drops of the present invention, it is preferred that the acidity or alkalinity is adjusted to about pH 4 to 9, particularly about pH 6 to 8, from the viewpoint of stability, ocular irritation and the like of the present compound contained therein. For adjusting the acidity or alkalinity, an aqueous sodium hydroxide solution, diluted hydrochloric acid and the like can be used according to a conventional method which is normally used for adjusting pH of eye drops but are not limited to this.

According to the present invention, there is provided a composition for eye drops comprising the present compound, which is stable for a long period of time and causes no ocular irritation. Thus, the composition of the present invention is effective for preventing and treating diabetic complication such as diabetic cataract, keratopathy, retinopathy and the like in the field of ophthalmology.

The following Experiments, Examples and Comparative Examples further illustrate the present invention in detail.

EXPERIMENT 1

Stability of the Present Compound by the Addition of Cyclodextrin

The present compound was dissolved in a phosphate buffer solution (pH 6.5) so that its concentration became 0.2 W/V %. Then, to this solution was added β-cyclodextrin so that the concentration became 0.4 W/V %, 0.75 W/V % or 1.5 W/V % to obtain three solutions. These solutions were filled into glass bottles and stored at 60° C., respectively to evaluate the stability. The results are shown in Table 1.

TABLE 1

| Storage period | Residual content (%) of the present compound β-cyclodextrin (W/V %) | | | |
|---|---|---|---|---|
|  | 0 | 0.4 | 0.75 | 1.5 |
| 1 week | 87.8 | 92.9 | 94.4 | 96.2 |
| 2 weeks | 77.6 | 85.3 | 89.6 | 93.4 |
| 3 weeks | 71.0 | 82.2 | 88.2 | 91.4 |

As is seen from the results of Table 1, the present compound in the buffer solution is stabilized by the addition of β-cyclodextrin.

EXPERIMENT 2

Ocular Irritation Test

The compositions prepared according to Examples 1 to 5 and Comparative Examples described hereinafter were applied to 10 healthy men, respectively to compare the degree of ocular irritation.

EXAMPLE 1

| The present compound | 0.05 g |
|---|---|
| Sodium chloride | 0.9 g |
| α-Cyclodextrin | 1.0 g |
| Sodium hydroxide | suitable amount |
| Sterile purified water | up to 100 ml |

To sterile purified water were added the present compound, sodium chloride and cyclodextrin to dissolve them and the mixture was adjusted to pH 6.5 with sodium hydroxide. Then, sterile purified water was further added to adjust the total volume to 100 ml, which was filtered using a 0.22 μm membrane filter to obtain the desired composition for eye drops.

EXAMPLES 2 to 4 AND COMPARATIVE EXAMPLES 1 AND 2

According to the same procedure as that described in Example 1, the composition of Example 2 was obtained except that β-cyclodextrin (1.0 g) was used instead of α-cyclodextrin (1.0 g). Likewise, the composition of Example 3 was obtained except that γ-cyclodextrin (1.0 g) was used instead of α-cyclodextrin (1.0 g) of Example 1. The composition of Example 4 was obtained except that polyvinyl pyrrolidone (average molecular weight: 40,000; 1.0 g) was used instead of α-cyclodextrin (1.0 g) of Example 1. The composition of Comparative Example 1 was obtained except that sodium hydrogensulfite (0.5 g) was used instead of α-cyclodextrin (1.0 g) of Example 1. Further, the composition of Comparative Example 2 was obtained except that α-cyclodextrin was eliminated from Example 1.

The results of the ocular irritation test which was carried out by using each composition described above are shown in Table 2. The numerical value used in Table 2 means the degree of irritation on application which is scored according to the following criteria.

0: no irritation and no unpleasant feeling
1: slightly irritated
2 to 3: irritated
4: extremely irritated
5: unbearably irritated

TABLE 2

| | Ocular irritation test (I) | | | | | |
|---|---|---|---|---|---|---|
| | Example No. | | | | Comp. Example No. | |
| Person No. | 1 | 2 | 3 | 4 | 1 | 2 |
| 1 | 4 | 0 | 2 | 4 | 5 | 4 |
| 2 | 5 | 1 | 3 | 3 | 5 | 4 |
| 3 | 5 | 1 | 4 | 5 | 5 | 5 |
| 4 | 3 | 0 | 2 | 4 | 4 | 4 |
| 5 | 4 | 0 | 2 | 4 | 4 | 4 |
| 6 | 4 | 0 | 3 | 5 | 5 | 4 |
| 7 | 4 | 0 | 2 | 4 | 4 | 4 |
| 8 | 5 | 1 | 3 | 5 | 5 | 5 |
| 9 | 4 | 0 | 2 | 4 | 4 | 4 |
| 10 | 4 | 1 | 4 | 5 | 4 | 5 |
| Average | 4.2 | 0.4 | 3.0 | 4.3 | 4.5 | 4.3 |

As is seen from these results, the addition of cyclodextrin, particularly β-cyclodextrin is effective for alleviating irritation on application of eye drops.

EXPERIMENT 3

Effect for Preventing Formation of Insoluble Matter

By using the compositions of Examples 5 to 7 and Comparative Example 3, severe test was carried out.

EXAMPLE 5

| | |
|---|---|
| The present compound | 0.2 g |
| β-Cyclodextrin | 0.9 g |
| Monosodium phosphate | 0.6 g |
| Disodium edetate | 0.1 g |
| Sodium hydroxide | suitable amount |
| Sterile purified water | up to 100 ml |

To sterile purified water were added the present compound, β-cyclodextrin, monosodium phosphate and disodium edetate to dissolve them and the mixture was adjusted to pH 7 with sodium hydroxide. Then, sterile purified water was further added to adjust the total volume to 100 ml, which was filtered using a 0.22 μm membrane filter to obtain the desired composition.

EXAMPLES 6 AND 7 AND COMPARATIVE EXAMPLE 3

According to the same procedure as that described in Example 5, the composition of Example 6 was obtained except that polyvinyl pyrrolidone (average molecular weight: 40,000; 2 g) was used instead of disodium edetate (0.1 g). Likewise, the composition of Example 7 was obtained except that polyvinyl pyrrolidone (average molecular weight: 40,000; 2 g) was added to the composition of Example 5. Further, the composition of Comparative Example 3 was obtained except that disodium edetate was not added in Example 5.

The compositions prepared according to the above Example 5 to 7 and Comparative Example 3 were filled into glass bottles and stored at 80° C. and 60° C. respectively. Then, the formation of insoluble matter was observed. The results are shown in Table 3.

TABLE 3

| Foreign insoluble matter test | | | | |
|---|---|---|---|---|
| | Example No. | | | |
| Storage conditions | 5 | 6 | 7 | Comp. Example 3 |
| 80° C., 1 day | + | − | − | + |
| 3 days | + | ± | − | + |
| 7 days | + | + | − | ++ |
| 60° C., 1 week | + | − | − | + |
| 2 weeks | + | ± | ± | + |
| 3 weeks | + | ± | ± | + |

(Note) Each symbol means as follows:
−: No insoluble matter was observed.
±: Only a little insoluble matter was observed.
+: Insoluble matter was slightly observed.
++: Relatively large amount of insoluble matter was observed.

As is seen from the above results, in the composition for eye drops containing neither disodium edetate nor polyvinyl pyrrolidone, relatively large amount of the insoluble matter is formed and, when either of them is formulated, the amount of the insoluble matter formed is relatively decreased and, further, when both of them are added, it is stable even under severe conditions.

EXPERIMENT 4

Effect of Preservative on Ocular Irritation

EXAMPLE 8

| | |
|---|---|
| The present compound | 0.2 g |
| β-Cyclodextrin | 0.9 g |
| Sodium chloride | 0.9 g |
| Benzalkonium chloride | 0.005 g |
| Sodium hydroxide | suitable amount |
| Sterile purified water | up to 100 ml |

To sterile purified water were added the present compound, β-cyclodextrin, sodium chloride and benzalkonium chloride to dissolve them and the mixture was adjusted to pH 7 with sodium hydroxide. Then, sterile purified water was further added to adjust the total volume to 100 ml, which was filtered using a 0.22 μm membrane filter to obtain the desired composition.

EXAMPLES 9 TO 15

According to the same procedure as that described in Example 8, the composition of Example 9 was obtained except that chlorobutanol (0.3 g) was used instead of benzalkonium chloride (0.005 g). Likewise, the composition of Example 10 was obtained except that phenethyl alcohol (0.5 g) was used instead of benzalkonium chloride (0.005 g) in Example 8. The composition of Example 11 was obtained except that benzyl alcohol (0.5 g) was used instead of benzalkonium chloride (0.005 g) in Example 8. The composition of Example 12 was obtained except that thimerosal (0.001 g) was used instead of benzalkonium chloride (0.005 g) in Example 8. The composition of Example 13 was obtained except that sorbic acid (0.1 g) was used instead of benzalkonium chloride (0.005 g) in Example 8. The composition of Example 14 was obtained except that methyl paraoxybenzoate (0.026 g) and propyl paraoxybenzoate (0.014 g) were used instead of benzalkonium chloride (0.005 g) in Example 8. The composition of Example 15 was obtained except that boric acid (2.0 g) was used instead of benzalkonium chloride (0.005 g) and sodium chloride was eliminated in Example 8.

The compositions produced according to Examples 8 to 15 were applied to 10 healthy men, respectively to compare the degree of ocular irritation. The results are shown in Table 4.

TABLE 4

Ocular irritation test (II)

| Person No. | Example No. | | | | | | | |
|---|---|---|---|---|---|---|---|---|
| | 8 | 9 | 10 | 11 | 12 | 13 | 14 | 15 |
| 1 | 0 | 1 | 5 | 5 | 0 | 2 | 4 | 0 |
| 2 | 1 | 2 | 4 | 4 | 1 | 3 | 4 | 1 |
| 3 | 1 | 2 | 4 | 4 | 1 | 4 | 4 | 0 |
| 4 | 1 | 3 | 4 | 4 | 1 | 4 | 4 | 0 |
| 5 | 2 | 4 | 5 | 5 | 2 | 4 | 5 | 1 |
| 6 | 1 | 2 | 4 | 4 | 0 | 3 | 4 | 0 |
| 7 | 0 | 1 | 3 | 3 | 0 | 2 | 3 | 0 |
| 8 | 1 | 2 | 4 | 4 | 1 | 3 | 5 | 0 |
| 9 | 1 | 2 | 4 | 4 | 1 | 3 | 4 | 0 |
| 10 | 2 | 3 | 4 | 5 | 1 | 4 | 5 | 1 |
| average | 1.0 | 2.2 | 4.1 | 4.2 | 0.8 | 3.2 | 4.2 | 0.3 |

(Note) The numerical values in Table 4 are the same as those of Table 2

As is seen from the above results, it is preferred to use boric acid, thimerosal or benzalkonium chloride as an preservative. It, is found that chlorobutanol, sorbic acid, phenethyl alcohol, paraoxybenzoate esters, benzyl alcohol and the like can be used as the preservative, in addition to these compounds.

EXPERIMENT 5

Stability Test

EXAMPLE 16

| | |
|---|---|
| The present compound | 0.2 g |
| β-Cyclodextrin | 0.9 g |
| Polyvinyl pyrrolidone | 2.0 g |

-continued

| | |
|---|---|
| Disodium edetate | 0.1 g |
| Sodium chloride | 0.9 g |
| Benzalkonium chloride | 0.005 g |
| Sodium hydroxide | suitable amount |
| Sterile purified water | up to 100 ml |

To sterile purified water was added the present compound, β-cyclodextrin, polyvinyl pyrrolidone, disodium edetate, sodium chloride and benzalkonium chloride to dissolve them and the mixture was adjusted to pH 7.5 with sodium hydroxide. Then, sterile purified water was further added to adjust the total volume to 100 ml, which was filtered using a 0.22 μm membrane filter to obtain the desired composition for eye drops.

EXAMPLES 17 AND 18

According to the same manner as that described in Example 16, the composition of Example 17 was obtained except that thimerosal (0.001 g) was used instead of benzalkonium chloride. Likewise, the composition of Example 18 was obtained except that boric acid (2.0 g) and borax (1.0 g) were used instead of sodium chloride and benzalkonium chloride in Example 16.

The compositions prepared in Example 16 to 18 were filled into glass bottles and stored at 40° C. for 1 month, respectively. Then, the formation of insoluble matter and stability of the present compound were tested and the results are shown in Table 5.

TABLE 5

Stability test

| | Example No. | | |
|---|---|---|---|
| | 16 | 17 | 18 |
| Formation of insoluble matter | ± | — | — |
| Residual content of the present compound (%) | 99.8 | 99.2 | 100.1 |

(Note) The symbols in Table 5 are the same as those of Table 3.

As is seen from the above results, in either of Examples of 16 to 18, little formation of insoluble matter is observed. Further, any degradation of the present compound is scarcely observed and the composition is stable.

What is claimed is:

1. A composition for the prevention and treatment of diabetic complications in the form of eye drops comprising as a main effective component a therapeutically effective amount of 3,4-dihydro-2,8-diisopropyl-3-thioxo2H-1,4-benzoxazine-4-acetic acid or a pharmaceutically acceptable salt thereof and 0.005 to 5 w/v % of β-cyclodextrin.

2. A composition according to claim 1, wherein the composition further comprises 0.2 to 20 w/v % of polyvinyl pyrrolidone having an average molecular weight of 25,000 to 120,000.

3. A composition according to claim 2, wherein the composition further comprises 0.01 to 1 w/v % of sodium edetate.

4. A composition according to claim 3, wherein the composition further comprises 0.2 to 4 w/v % of boric acid.

* * * * *